United States Patent [19]

Wilson

[11] 4,149,014
[45] Apr. 10, 1979

[54] PROCESS FOR THE PREPARATION OF BIS-(β-CARBOXYETHYL)ALKYL PHOSPHINE OXIDES FROM TRIS-CYANOETHYL PHOSPHINE

[75] Inventor: Glenn R. Wilson, Pensacola, Fla.

[73] Assignee: Monsanto Company, St. Louis, Mo.

[21] Appl. No.: 780,563

[22] Filed: Mar. 23, 1977

[51] Int. Cl.$^2$ .............................................. C07F 9/53
[52] U.S. Cl. ................................ 562/594; 260/465.6; 260/465.8 R
[58] Field of Search ................... 260/537 S, 465.8 R; 562/594

[56] References Cited

U.S. PATENT DOCUMENTS 3,784,638   1/1974   Lambert ........................... 260/537 S

*Primary Examiner*—Vivian Garner
*Attorney, Agent, or Firm*—Thomas Y. Awalt, Jr.

[57] ABSTRACT

Lower alkyl bis-(β-carboxyethyl) phosphine oxides are prepared from tris-cyanoethyl phosphine in a functionally coordinated sequentially ordered process comprising alkylating the tris-cyanoethyl phosphine to a phosphonium salt, dequarternizing the phosphonium salt to a lower alkyl bis-(β-cyanoethyl) phosphine, oxidizing the phosphine to phosphine oxide, hydrolyzing the phosphine oxide with calcium hydroxide to produce a calcium salt of lower alkyl bis-(β-carboxyethyl) phosphine oxide, and acidifying the calcium salt to produce lower alkyl bis-(β-carboxyethyl) phosphine oxide.

9 Claims, No Drawings

PROCESS FOR THE PREPARATION OF BIS-(β-CARBOXYETHYL)ALKYL PHOSPHINE OXIDES FROM TRIS-CYANOETHYL PHOSPHINE

BACKGROUND OF THE INVENTION

Lower alkyl bis-(β-carboxyethyl) phosphine oxides are well known to be useful as fire retardant additives, especially for polymers. They are commonly prepared from tris-cyanoethyl phosphine in laboratory quantities using an arduous five-step procedure summarized as follows (with methyl representing the lower alkyl):

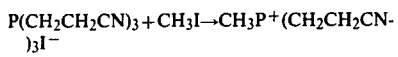  (1)

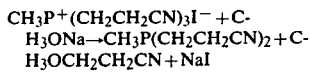  (2)

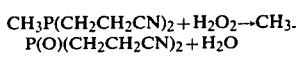  (3)

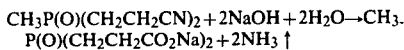  (4)

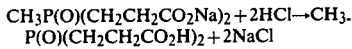  (5)

With respect to three of the first four reactions, it was necessary to separate the desired component from the reaction mix prior to its use in the following reaction; and in the case of the last reaction, the phosphine oxide product was isolated only with difficulty. For example, reaction (1) was carried out in acetic acid with a 50% excess of methyl iodide, and the intermediate, high-melting point, insoluble phosphonium salt was filtered off and dried under vacuum to remove any traces of acetic acid. In step (2) the dried phosphonium salt was suspended in methanol before addition of sodium methoxide; and the reaction product was concentrated to remove the methanol solvent. It was necessary to repeatedly extract the residue of reaction (2) with benzene or toluene to obtain a crude product suitable for use in step (3). In step (3) the crude product of reaction (2) was dissolved in acetic acid, and hydrogen peroxide (diluted with acetic acid) was added cautiously, the reaction being violently exothermic. The reaction product of step (3) was thereafter concentrated to remove the last traces of acetic acid, and the residue of the concentration was used in step (4). In step (5), the hydrolysis mixture from step (4) was acidified to a pH of 2 with concentrated hydrochloric acid, and the mixture was concentrated. Upon cooling, the crude product, which contained as much as 20% sodium chloride, precipitated out and was filtered off, usually requiring two recrystallizations from water. The overall yield of polymerization grade phosphine oxide was 40-45% of the calculated yield.

Improvements over the above described process included a combination of the oxidation and hydrolysis steps (3) and (4) into a single step of a much improved process; but it was found with respect to the improved process that isolation of the phosphine oxide product was difficult to achieve on a commercial scale.

Particularly in view of the current industrial need for large quantities of this class of phosphine oxides a practical process for its production is needed. If the number of process (reaction) steps cannot be substantially reduced (an effort in which no practical advances have been made), the art may be advanced by eliminating requirements for repeated and complicated separation procedures. A combination of otherwise equivalent (to the prior art) reactions coordinated in such a manner that the reaction product mixtures, or easily separable components thereof, of preceeding reactions can be employed as such in the next subsequent reaction without the need for complicated separation procedures, would represent a significant advance in the art and constitutes a primary object of this invention.

SUMMARY OF THE INVENTION

According to the present invention, lower alkyl bis-(β-carboxyethyl) phosphine oxide is produced from triscyanoethyl phosphine by the following functionally coordinated sequentially ordered reaction steps:

(a) preparing a lower alkyl phosphonium salt of tris-(β-cyanoethyl) phosphine by alkylating tris-(β-cyanoethyl) phosphine with a lower alkyl sulfate;

(b) dequaternizing the phosphonium salt of tris-cyanoethyl phosphine with methanolic potassium hydroxide to produce a first reaction mixture including lower alkyl bis-(β-cyanoethyl) phosphine and a first precipitate being a lower alkyl potassium sulfate;

(c) separating the first precipitate from the remainder of the first reaction mixture;

(d) oxidizing the lower alkyl bis-(β-cyanoethyl) phosphine in the remainder of the first reaction mixture with hydrogen peroxide thereby to produce a second reaction mixture including lower alkyl bis-(β-cyanoethyl) phosphine oxide;

(e) hydrolyzing the lower alkyl bis-(β-cyanoethyl) phosphine oxide with a surplus of calcium hydroxide in the presence of the second reaction mixture thereby to produce a calcium salt of lower alkyl bis-(β-carboxyethyl) phosphine oxide and ammonia in a third reaction mixture;

(f) acidifing the third reaction mixture with sulfuric acid thereby to produce lower alkyl bis-(β-carboxyethyl) phosphine oxide in a fourth reaction mixture including insoluble calcium sulfate as a second precipitate; and (g) separating the lower alkyl bis-(β-carboxyethyl) phosphine oxide from the second precipitate.

One advantage of this invention is that steps (a) and (b) can be carried out in the same solvent (methanol) thus eliminating the extra steps of isolating and drying the intermediate phosphonium salt.

It is another advantage of this invention that by using potassium hydroxide instead of sodium methoxide for dequarternizing (step b), a precipitate (a lower alkyl potassium sulfate), crystallizes out and is readily filtered from the reaction mixture thus eliminating the concentration and multiple extraction steps required in the above described prior art process for removing potassium iodide.

Yet another advantage lies in the use of inexpensive ingredients such as dimethylsulfate and calcium hydroxide in lieu of methyl iodide and sodium or barium hydroxide, such economy strongly affecting the commercial practicality of the process.

DESCRIPTION OF THE PREFERRED EMBODIMENT

A preferred embodiment is in accordance with the following reaction sequence (the reactions also being subsequently referred to as the associated steps) in which the lower alkyl is methyl.

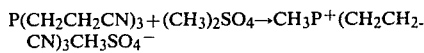  (1a)

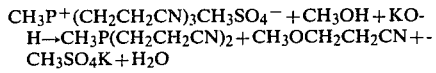  (2a)

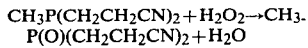  (3a)

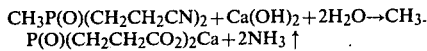  (4a)

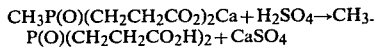  (5a)

Unless otherwise indicated, percentages are by weight.

Any lower alkyl sulfate is suitable for use in preparing the insoluble phosphonium salt of step (1a). By lower alkyl is meant an alkyl having not more than about 6 carbon atoms, e.g., methyl or ethyl. The step (1a) reaction is preferably carried out in methanol rather than acetic acid, and the intermediate phosphonium salt in the reaction product of step (1a) need not be isolated from the entire reaction mixture which is used as the starting material for step (2a). In step (2a), methanolic potassium hydroxide is added at room temperature to the reaction mixture from step (1a). [The potassium hydroxide is much favored over the hydroxides of other alkali metals which have a tendency to form gelatenous sulfates.] The methyl potassium sulfate that precipitates out in step (2a) (which is in a crystalline form especially suitable for filtration) is filtered off and the filtrate is used as the starting material for step (3a) (there is no need for isolating any intermediate; and the concentration and extraction steps of the prior art are thereby eliminated). The methanolic filtrate from step (2a) is then diluted with water, and hydrogen peroxide (diluted with water) is added preferably at a rate so that the temperature does not exceed 50° C. Although exothermic, the step (3a) reaction is not so violent as in the case of the non-methanolic equivalent reaction of the prior art. There is no need to remove an acidic solvent as was necessary in the processes heretofore known. The aqueous residue from step (3a) is combined with calcium hydroxide under reaction conditions, preferably in an autoclave, with agitation, and heat of about 160°–180° C. for about 3–4 hours, at a pressure of about 190–300 psig (144115–221445 kg per sq meter) while bleeding ammonia. Atmospheric pressure may be used for the refluxing with calcium hydroxide, but the reaction is infinitely slow. With the addition of a small quantity of sodium hydroxide, an atmospheric pressure hydrolysis may be completed within about 48 hours. Choice of the calcium hydroxide in step (4a) is dictated by the properties of the precipitate of the reaction of step (5a). It has been found, for example, that in the reaction media of (5a), calcium sulfate (unlike most other metal sulfates which increase in solubility with temperature) is less soluble when the temperature is increased, a phenomenon which favors the reaction and facilitates recovery of the phosphine oxide.

The reaction product mixture of step (4a) is acidified to a pH of about 2.0 with sulfuric acid, and the insoluble calcium sulfate that forms is filtered off, whereupon the filtrate is thereafter concentrated to precipitate the crude lower alkyl bis-($\beta$-carboxyethyl) phosphine oxide. This precipitate is ordinarily 95% pure; and after one recrystallization has a polymerization grade purity of about 99%. The overall yield of this polymerization grade bis-($\beta$-carboxyethyl) phosphine oxide is about 65% of the calculated yield.

EXAMPLES

All atmospheric pressure reactions were carried out in 3-neck Pyrex flasks equipped with a stirring assembly (Teflon paddle-type stirrer), condenser, dropping funnel, thermometer, $N_2$ purge inlet and outlet and a heating mantle or ice bath.

For pressurized reactions, a 300 ml or one-liter, stainless steel autoclave was used.

All percentages described were by weight unless otherwise indicated.

All reactions were carried out in well-ventilated hoods. Dimethyl sulfate (DMS) is an extremely toxic reagent (recently classified as a carcinogen) and every precaution was taken to avoid exposure of skin and respiration to vapors.

A nitrogen purge (blanket) was used with reaction mixtures involving the use or formation of a tertiary phosphine to prevent air oxidation. [Air oxidation of selected tertiary phosphines indicated that oxidation is not selective for the phosphorus moiety but also includes free-radical oxidations of hydrocarbon side chains.]

EXAMPLE 1

[illustrating by way of a preferred embodiment, the production of methyl bis-($\beta$-carboxyethyl) phosphine oxide (with the reaction of step (4a) being conducted at atmospheric pressure)]

A 6-liter, 3-neck Pyrex flask (equipped with a stirring assembly, condenser, dropping funnel, immersion thermometer, $N_2$ purge inlet and outlet and heating mantle) was charged with 966 g (4.74 mole) of tris-($\beta$-cyanoethyl) phosphine (TCEP) (94.8% purity) and 1875 ml of methanol. The system was purged with $N_2$ and the mixture stirred and warmed to ca 60° C. and the heat turned off. DMS, 630.6 g (5.0 moles) was added to the stirred suspension of TCEP at a rate that maintained moderate refluxing of the methanol (reaction is very exothermic). When all the DMS had been added, 1500 ml of methanol were distilled from the reaction mixture, the residue cooled to room temperature and a solution of 322.4 g (5.0 moles) of 87% KOH in 1500 ml of methanol added rapidly to the stirred residue. The mixture was stirred at a temperature of 21° C. for one hour during which time crystalline $CH_3SO_4K.\frac{1}{2}H_2O$ precipitated out. The salt was filtered off under a $N_2$ blanket and washed with 300 ml of fresh methanol. The filtrate and wash were combined in a 12-liter, 3-neck flask (equipped with a stirrer, condenser, dropping funnel and $N_2$ purge), diluted with 1200 ml of water and a solution of 567 g of 30% hydrogen peroxide in 500 ml of water added with external cooling to keep the temperature below 50° C. When all the hydrogen peroxide had been added, the methanol was distilled out. The aqueous reaction mixture was hydrolyzed by adding 555 g (7.49 moles) of $Ca(OH)_2$, 30 g (0.75 mole) of NaOH, and 300 ml of water and refluxed until ammonia evolution ceased (ca 48 hours). The hydrolysis mixture was cooled to room temperature and acidified to pH 2.0 with sulfuric acid (ca 457 ml of concentrated sulfuric acid diluted with an equal volume of water). The resulting mixture was extremely viscous. It was diluted with 1500 ml of water, stirred and heated to reflux and filtered hot to remove the insoluble CaSO$_4$. The filtrate was concentrated to 3500 ml, filtered hot to remove additional CaSO$_4$, the filtrate further concentrated to 1500 ml and allowed to cool to room temperature. The crude methyl bis-($\beta$-carboxyethyl) phosphine oxide (CEMPO) that precipitated was filtered off, washed with 300 ml of ice water, 500 ml of acetone and dried at 110° C. under vacuum (oil pump). The dried CEMPO weighed 654.5 g, melted at 172°–174° C. and had a purity of 99.7% (titration with 0.1N NaOH). The net yield of CEMPO was 66.1% of the calculated theoretical yield based upon the starting material, TCEP.

Although the hydrolysis required 48 hours for completion, without the added NaOH the rate is infinitely slow due to the low solubility and inverse solubility/temperature relationship of Ca(OH)$_2$. The use of NaOH also introduces a water-soluble salt into the last step. If this is undesirable, the NaOH can be replaced with an equivalent quantity of Ba(OH)$_2$.

EXAMPLE 2

[illustrating by way of a preferred embodiment, production of the same phosphine oxide (with the reaction of step (4a) being conducted under pressure)]

The starting material was the methanolic filtrate (of Example 1) after filtering off the CH$_3$SO$_4$K from the KOH dequaternization of methyl tris-($\beta$-cyanoethyl) phosphonium methyl sulfate. The quantity of filtrate used was 425 g and it contained a total of 0.586 mole of tertiary phosphine (iodometric titration).

The sample was diluted with 300 ml of water and oxidized by adding 67.1 g (0.593 mole) of 30% hydrogen peroxide diluted with 75 ml of water (temperature was kept below 50° C.). The resulting solution was distilled to remove methanol and the aqueous residue charged into a 1-liter, 316 stainless steel autoclave (equipped with a stirrer and condenser arranged for venting gases from the autoclave) together with 96.9 g (1.31 mole) of Ca(OH)$_2$. The autoclave was heated as follows with periodic pressuring with N$_2$ to permit attaining higher temperatures.

TABLE 1

| TIME (Hrs.) | REACTION TEMPERATURE ° C. | PRESSURE, psig | PRESSURE, kg/m$^2$ |
|---|---|---|---|
| 0 | | 50 (N$_2$) | 45695 |
| 0.92 | 148 | 105 | 84360 |
| 1.0 | 158 | 130/200 (N$_2$) | 101935/151145(N$_2$) |
| 1.25 | 170 | 235 | 175750 |
| 1.33 | 173 | 235 | 175750 |
| 1.38 | 175 | 235 | 175750 |
| 1.50 | 180 | 245 | 182780 |
| 1.58 | 180 | 240 | 179265 |
| 1.70 | 180 | 235/300 (N$_2$) | 175750/221445(N$_2$) |
| 2.25 | 185 | 260 | 193325 |
| 2.38 | 182 | 240 | 179265 |
| 2.60 | 185 | 236 | 176453 |
| 2.78 | 185 | 220 | 165205 |
| 2.92 | 187 | 215 | 161690 |
| 3.08 | 187 | 200/250 (N$_2$) | 151145/186295(N$_2$) |
| 3.25 | 190 | 200 | 151145 |
| 3.42 | 190 | 200/250 (N$_2$) | 151145/186295(N$_2$) |
| 3.50 | 190 | 200 | 151145 |

The autoclave was cooled, the contents drained, acidified to pH 2.0 with sulfuric acid (184 ml ca 50% sulfuric), heated to reflux and the CaSO$_4$ filtered from the hot solution. The filtrate weighed 1091.3 g. A sample of the filtrate was removed for analysis and was found to contain 9.97% CEMPO and 0.99% P(O)(CH$_2$CH$_2$CO$_2$H)$_3$. The combined yield of carboxylic acid (1.167 equivalents) agrees very well with the 1.172 equivalents of tertiary phosphines in the initial charge.

The total quantity of ammonia liberated (1.114 mole) is 95% of the calculated quantity based upon the tertiary phosphine content before hydrolysis.

The remainder of the filtrate (1080.5 g) was treated with activated charcoal, concentrated to 250 ml and cooled to room temperature. The crude CEMPO that precipitated was filtered off, washed with acetone and dried. The product weighed 100.5 g and titration indicated a purity of 90.4%. This indicated 64.3% recovery of CEMPO synthesized.

The use of pressure can be made to reduce hydrolysis time from 48 hours (atmospheric pressure) to only 3–4 hours.

EXAMPLES 3–6

The following four examples show the effect of variations in stoichiometries and conditions of dequaternization. Except as indicated in Table 2, the conditions of dequaternization are as described in Example 1.

TABLE II

| Example Number | REACTANTS MOLES P(CH$_2$CH$_2$CN)$_3$ | (CH$_3$)$_2$SO$_4$ | KOH | CONDITIONS | CH$_3$P(CH$_2$CH$_2$CN)$_2$$^+$ Moles | % THEO. |
|---|---|---|---|---|---|---|
| 3 | 0.974 | 0.95 | 0.95 | A | .773 | 79.0 |
| 4 | 4.87 | 4.75 | 4.75 | B | 3.31 | 68.0 |
| 5 | 0.974 | 1.04 | 1.04 | C | .707 | 72.6 |
| 6 | 0.974 | 0.95 | 0.95 | D | .798 | 81.9 |

May contain 0–2% P(CH$_2$CH$_2$CN)$_3$

A - KOH added rapidly at room temperature. Heated to 40° C. and cooled.
B- KOH added rapidly at room temperature. Refluxed one hour.
C- KOH added rapidly at room temperature. Stirred one hour at room temperature.
D- KOH added at room temperature in 20 minutes. Heated to 40° C. and cooled.

Higher yields of methyl bis-($\beta$-cyanoethyl) phosphine were obtained when the dequarternization was carried out at room temperature on reaction mixtures prepared from a slight deficiency of DMS and KOH. The rate of addition of KOH had no significant affect on the yield. Lower yields were obtained when an excess of DMS and KOH were employed or where dequarternization was carried out at reflux temperature with slight deficiencies of DMS and KOH.

I claim:
1. Process for the preparation of lower alkyl bis-(β-carboxyethyl) phosphine oxide from tris-cyanoethyl phosphine comprising sequentially:
 (a) preparing a lower alkyl phosphonium salt of tris-cyanoethyl phosphine by alkylating tris-cyanoethyl phosphine with a lower alkyl sulfate;
 (b) dequaternizing the phosphonium salt of tris-cyanoethyl phosphine with methanolic potassium hydroxide to produce a first reaction mixture including lower alkyl bis-(β-cyanoethyl) phosphine and a first precipitate being a lower alkyl potassium sulfate;
 (c) separating the first precipitate from the remainder of the first reaction mixture;
 (d) oxidizing the lower alkyl bis-(β-cyanoethyl) phosphine in the remainder of the first reaction mixture with hydrogen peroxide thereby to produce a second reaction mixture including lower alkyl bis-(β-cyanoethyl) phosphine oxide;
 (e) hydrolyzing the lower alkyl bis-(β-cyanoethyl) phosphine oxide with a surplus of calcium hydroxide in the presence of the second reaction mixture thereby to produce a calcium salt of lower alkyl bis-(β-carboxyethyl) phosphine oxide and ammonia in a third reaction mixture;
 (f) acidifying the third reaction mixture with sulfuric acid thereby to produce lower alkyl bis-(β-carboxyethyl) phosphine oxide in a fourth reaction mixture including a second precipitate being insoluble calcium sulfate; and
 (g) separating the lower alkyl bis-(β-carboxyethyl) phosphine oxide from the second precipitate.

2. The process of claim 1 wherein the lower alkyl bis-(βcarboxyethyl) phosphine oxide is methyl bis-(β-carboxyethyl) phosphine oxide, and the alkylating agent is dimethyl sulfate.

3. The process of claim 1 wherein the lower alkyl bis-(β-carboxyethyl) phosphine oxide is ethyl bis-(β-carboxyethyl) phosphine oxide and the alkylating agent is diethylsulfate.

4. The process of claim 1 wherein step (a) is conducted in a methanol solvent, and the starting material for step (b) is the lower alkyl phosphonium salt of tris-cyanoethyl phosphine in the same methanol solvent.

5. The process of claim 1 wherein step (e) is conducted at a pressure of 190–300 psig, at a temperature of 160°–180° C.

6. The process of claim 1 wherein step (e) is conducted at atmospheric pressure and the hydrolysis reaction step (e) further includes sodium hydroxide in the amount necessary to accelerate the reaction without substantially increasing the solubility of the precipitate of step (f) at the reaction temperature.

7. Process for the preparation of methyl bis-(β-carboxyethyl) phosphine oxide from tris-cyanoethyl phosphine comprising sequentially:
 (a) preparing a phosphonium salt of tris-cyanoethyl phosphine by alkylating tris-cyanoethyl phosphine with dimethylsulfate in a methanol medium;
 (b) dequaternizing the phosphonium salt of tris-cyanoethyl phosphine in the methanol medium with potassium hydroxide to produce a first reaction mixture including methyl bis-(β-cyanoethyl) phosphine and a first precipitate being methyl potassium sulfate;
 (c) separating the first precipitate from the remainder of the first reaction mixture;
 (d) oxidizing the methyl bis-(β-cyanoethyl) phosphine in the remainder of the first reaction mixture with hydrogen peroxide thereby to produce a second reaction mixture including methyl bis-(β-cyanoethyl) phosphine oxide;
 (e) hydrolyzing the methyl bis-(β-cyanoethyl) phosphine oxide with a surplus of calcium hydroxide in the presence of the second reaction mixture thereby to produce a calcium salt of methyl bis-(β-carboxyethyl) phosphine oxide and ammonia in a third reaction mixture;
 (f) acidifing the third reaction mixture with sulfuric acid thereby to produce methyl bis-(β-carboxyethyl) phosphine oxide in a fourth reaction mixture including a second precipitate being insoluble calcium sulfate; and
 (g) separating the methyl bis-(β-carboxyethyl) phosphine oxide from the second precipitate.

8. The process of claim 7 wherein step (e) is conducted under a pressure of 190–300 psig at a temperature of 160°–180° C.

9. The process of claim 7 wherein step (e) is conducted at atmospheric pressure and the hydrolysis reaction step (e) further includes sodium hydroxide in the amount necessary to accelerate the reaction without substantially increasing the solubility of the precipitate of step (f) at the reaction temperature.

* * * * *